United States Patent [19]

Barnes

[11] Patent Number: 5,785,526
[45] Date of Patent: Jul. 28, 1998

[54] METHOD FOR ADAPTING A CROWN TO AN EXISTING PARTIAL DENTURE

[75] Inventor: Alan D. Barnes, Highland, Mich.

[73] Assignee: Coaching For Service, Inc., Highland, Mich.

[21] Appl. No.: 865,293

[22] Filed: May 29, 1997

[51] Int. Cl.⁶ .......................... A61C 13/12; A61C 13/225
[52] U.S. Cl. ........................................ 433/178; 433/214
[58] Field of Search ............................ 433/37, 71, 178, 433/213, 214, 218, 219

[56] References Cited

U.S. PATENT DOCUMENTS

| | | | |
|---|---|---|---|
| 4,775,320 | 10/1988 | Marshall et al. | 433/214 |
| 4,917,605 | 4/1990 | Hallmark | 433/178 |
| 5,102,337 | 4/1992 | Soroca | 433/178 |

*Primary Examiner*—Nicholas D. Lucchesi
*Attorney, Agent, or Firm*—Alex Rhodes

[57] ABSTRACT

A method for adapting a crown to a clasp and rest of an existing partial denture without depriving a patient of the partial denture during the time the crown is being fabricated in a dental laboratory. The method comprises the steps of fabricating an accurate pick-up impression of the clasp and rest in a dentist's office, fabricating an accurate model of the clasp and rest in a dental laboratory, and incorporating the clasp and rest model in a model at the dental laboratory which is used for fabricating a crown. The fabrication of the accurate clasp and rest model by a dentist includes the important step of supporting the pick-up impression of the clasp and rest on a dimensionally stable coping over a tooth which has been prepared for the crown.

9 Claims, 2 Drawing Sheets

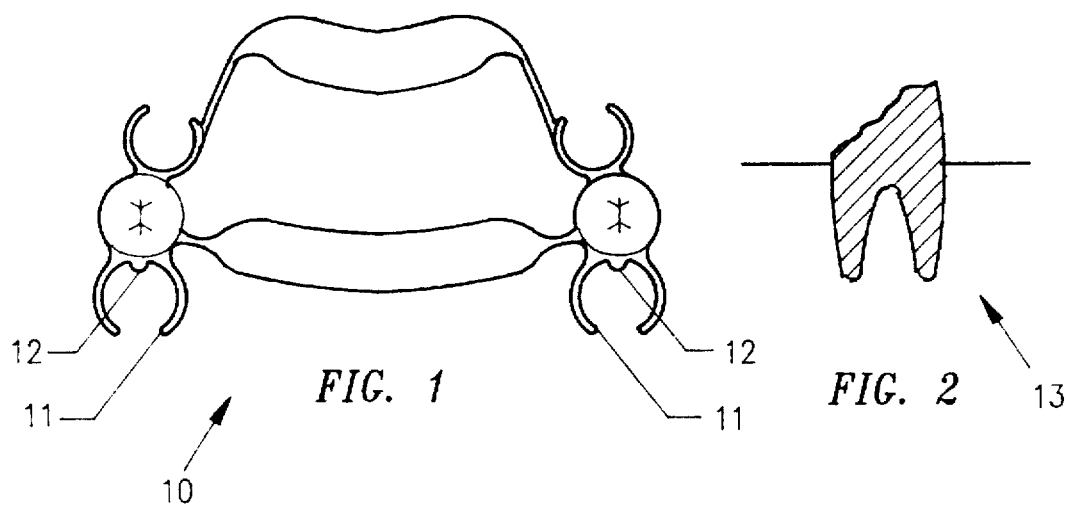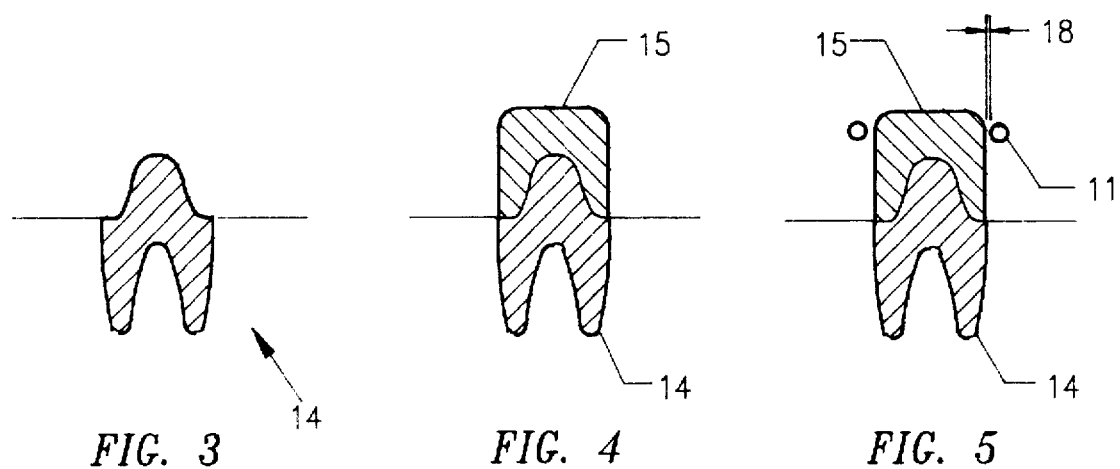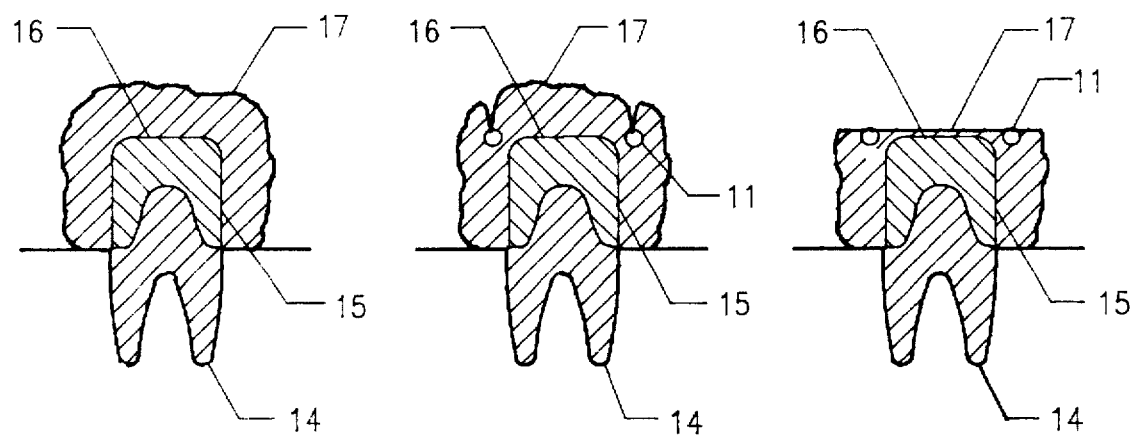

METHOD FOR ADAPTING A CROWN TO AN EXISTING PARTIAL DENTURE

FIELD OF THE INVENTION

This invention relates to the making and fitting of prosthetic devices and more particularly to adapting a crown to an existing partial denture.

BACKGROUND OF THE INVENTION

One of the major challenges in dentistry has been the adaptation of a new crown to a tooth which lies within the confines of an existing partial denture clasp. If the adaptation is not properly done, the tooth or partial denture may be destroyed, or excessive rework may be required, but most certaintly a patient will experience discomfort. Many attempts to adapt a crown to an existing partial without forwarding the partial denture to a dental lab have been made without success.

The current practice for adapting a crown to an existing partial denture which requires a dentist to forward the partial denture to a lab together with impressions of the patent's mouth is undesirable because of the following reasons. First, the patient's appearance is adversely affected while the partial is at the dental lab. This is particularly objectionable to women and men whose livelihood depends upon their relationships with others. Second, the eating ability of many patients is substantially impaired. Third, in the absence of the partial, teeth may chip or shift. Fourth, the patient must return to the dentist's office a number of times.

SUMMARY OF THE INVENTION

The present invention overcomes the above problems by eliminating the forwarding of the partial denture to the dental lab. Many attempts by others have been made to eliminate the forwarding of a partial denture to a dental lab without success. With the new method, the patient is not without the partial while the crown is being fabricated at the dental lab. Another benefit of the invention is that after the crown has been returned and seated no adjustments will be necessary to re-seat the partial.

The invention resides in its ability to fabricate at a dental lab a metal duplicate of a clasp and rest. The keys to this improvement are the use of a coping for fabricating a precise pick-up impression at a dentist's office and the fabrication of the metal duplicate at the dental lab. Suitable materials and procedures must be used for fabricating the coping and the pick-up impression in order to be successful in adapting the crown to the partial denture without supplying the partial denture to a dental lab.

Further benefits and features of the invention will become apparent from the ensuing detailed description and drawings which disclose the invention and the best mode which is contemplated in carrying out the invention. The property in which exclusive rights are claimed is set forth in each of the numbered claims at the conclusion of the detailed description.

BRIEF DESCRIPTION OF THE DRAWINGS

The invention will be better understood and further objects, characterizing features, details and advantages thereof will appear more clearly with reference to the diagrammatic drawings illustrating a presently preferred specific embodiment of the invention by way of non-limiting example only.

FIG. 1 is plan view of a partial denture.

FIG. 2 is a longitudinal cross-sectional view of a tooth in need of a crown.

FIG. 3 shows the tooth after it has been prepared by a dentist for the crown.

FIG. 4 shows the tooth after the addition of a coping.

FIG. 5 shows the tooth after the partial denture has been installed.

FIG. 6 shows the tooth after the partial denture has been removed and a polyvinyl material has been added to the coping for a pick-up impression.

FIG. 7 shows the tooth after a pick-up impression of the partial denture has been made.

FIG. 8 shows the tooth after a portion of the pick-up impression has been removed to expose a clasp and rest of the partial denture.

DESCRIPTION OF THE PREFERRED EMBODIMENT

Figures 9, 10:
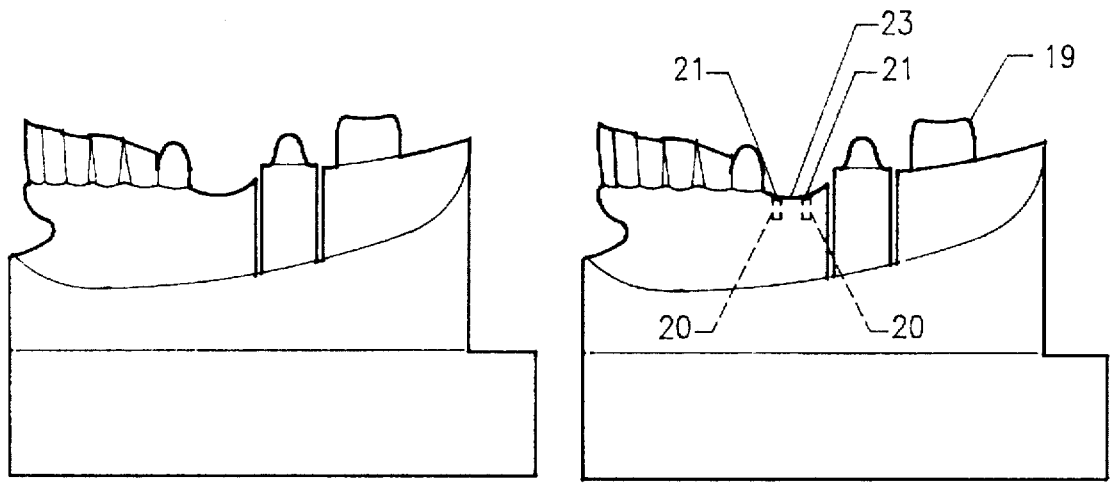
FIG. 9 is a left side view of a model of a crown preparation poured at a dental lab from a crown impression which is supplied by a dentist.
FIG. 10 is the crown model of FIG. 9 with two small holes in the saddle area of a missing tooth.

Referring now to the drawings, wherein like numerals designate like and similar parts throughout the several views, the best mode which is contemplated for carrying out my invention is embodied in a preferred sequence of steps at a dental office which are illustrated in FIGS. 3 through 8, inclusive.

FIG. 1 depicts a conventional partial denture 10 which is referred to herein for purposes of describing my invention. The partial denture 10 includes a pair of thin wire-like clasps 11, one of which surrounds the affected tooth and a pair of rests 12, one of which overlies the affected tooth. FIG. 2 depicts the affected tooth 13 which is in need of a crown (not shown).

The first step at the dental office is to remove the partial denture 10 and in the usual manner prepare the tooth 13 for a crown, the prepared tooth hereafter referred to as the "prep" 14. The tooth 13 is prepared in the usual manner by grinding away some of the tooth 13 to provide clearance and support for a crown (not shown). It is important that the prep 14 be carefully prepared to supply a suitable base for a coping 15 which is to be added.

After the tooth has been prepared for the crown, the usual crown impression (not shown) is taken for fabricating the crown and the usual bite impression (not shown) is taken insuring that the occlusial relationship between the patient's maxillary and mandibular arches is maintained by the dental lab during the fabrication of the crown.

The next step is to fabricate the coping 15, as shown in FIG. 4, over the prep, using a proper light cured composite material and a conventional spatula. The coping 15 serves as a foundation for a pick-up impression which will be later added over the coping 15. The lower portion of the coping 15 should be close to but should not extend beyond the lower margin of the prep. It is most important that the coping 15 seat properly on the prep. ie., the coping 15 must neither rock nor turn on the prep. The coping material must have high stability and minimum shrinkage. An exemplary material for the coping 15 is the light curing composite Kulzer's Dentacolor®. The material is a preparation of a light curing silicone dioxide and is supplied in convenient automix plunger syringes.

After the coping 15 is fabricated over the prep, it is checked for rocking or turning on the prep. If it neither rocks nor turns, the partial denture 10 is returned to the patient's mouth, as shown in FIG. 5, over the coping 15 and the clearance 18 between the coping 15 is checked. If there is not about 1 to 1.5 millimeters of clearance 18 between the clasp 11 and coping 15, the coping 15 is carefully trimmed to provide this amount of clearance 18.

The next step is to paint the coping 15 with a tray adhesive 16, making sure that the adhesive is compatible with the coping material. This step requires removal of the partial denture 10 and coping 15 from the patient's mouth. After the tray adhesive 16 is applied to the outer surface of the coping 15, it is allowed to dry. After about 1 to 1.5 minutes, excess adhesive 16, if any, is blown off the coping 15 and the coping 15 is returned to the patient's mouth without the partial denture 10.

The next step is to fabricate a pick-up impression 17 by dispensing a poylvinyl bite registration material over the coping 15 from an automix cartridge. The bite registration material should be soft in consistency when expressed from the cartridge and should become quite rigid when set up. Two polyvinyl bite registration materials which are exemplary of suitable materials are the Exacta® Products, Inc. Vinyl Polysiloxane and the 3M® 9304 Automixed Bite Registration Material. Both are supplied in convenient automix cartridges.

Referring to FIG. 6, a liberal amount of the polyvinyl material is applied over and all around the entire coping 15 to insure that the shape of the clasp 11 and rest 12 of the partial denture 10 will be completely picked up. By way of example of a proper amount, the bite registration material can be stacked up from 16 to 20 millimeters.

Almost immediately after the bite registration material has been applied, the partial denture 10 is placed back in the patient's mouth, as shown in FIG. 7, to completely embed the clasp 11 and rest 12 of the partial denture 10 into the polyvinyl pick-up impression 17. After the partial denture 10 has been placed in the patient's mouth, it is very important that the patient not bite down on the partial denture 10 or pick-up impression 17. Excessive force can disturb the gum tissues and/or the partial denture 10. Instead, the application of a light finger pressure to the partial denture 10 for about 2 to 2.5 minutes is preferred to allow the impression 17 sufficient time to cure.

After 2 to 2.5 minutes, the partial denture 10, is removed from the patient's mouth with the coping 15 and pick-up impression adhering to the partial 10. The partial denture 10 is then stripped from the pick-up impression 17 by carefully slicing away layers of the pick-up impression 17 with a sharp knife to expose the tops of the clasp 11 and rest 12 which are just sufficient to strip the clasp 11 and rest 12 from the pick-up impression 17. Thereafter, in the usual manner, a temporary crown is prepared and installed on the prep 14 and the partial denture 10 is returned to the patient's mouth for use during the time a permanent crown is being fabricated at the dental lab.

After the temporary crown and the partial denture 10 have been installed, the pick-up impression 17 and attached coping 15 are forwarded to the dental lab with the crown and bite impressions of the patient's mouth to fabricate the permanent crown.

When the impressions are received by the dental laboratory, a model 19 as shown in FIG. 9 is cast from the crown impression. After the crown model 19 is made, excess material is trimmed from the pick-up impression 17 which would interfere with the fabrication of a pattern for making a metal casting of the clasp 11 and rest 12. The pick-up impression 17 is then mounted on the crown model 19 and checked for movement on the crown model 19.

Referring now to FIG. 10, if no significant movement is detected between the pick-up impression 17 and the crown model 19, the pick-up impression 17 is removed and 2 small diameter parallel holes 20 are drilled with a 702 Fisher burr, about 2 to 3 mm apart and 1.5 mm deep in the saddle 23 of the crown model 19. The holes 20 are preferably countersunk 21 with a #8 round burr to insure that there will be a positive seat for a fabricated metal model 22 of the clasp 11 and rest 12 which will be described in proper sequence.

Figures 11, 12:
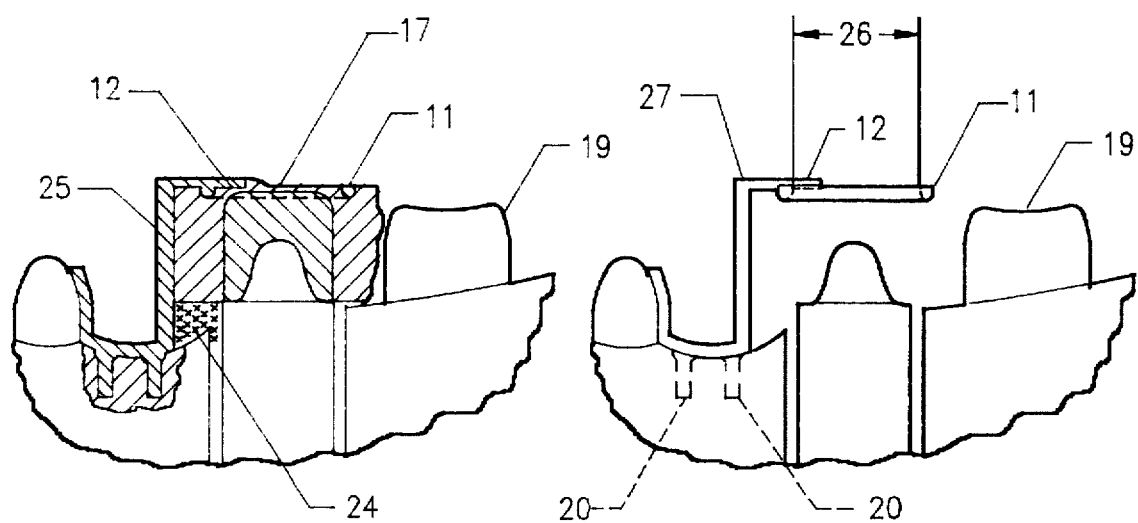
FIG. 11 is an enlarged fragmentary view showing the crown model in partial section, the pick-up impression of the clasp and rest mounted on the prep portion of the crown model, and a pattern for making a metal casting of the clasp and rest.
FIG. 12 is the enlarged fragmentary view showing the crown model and metal casting of the clasp and rest mounted on the crown model and over the crown preparation.

After the countersinking of the holes 20, the crown model 19 is prepared for making a pattern 25 of the clasp 11 and rest 12 by sealing voids and gaps with wax 24. The pick-up impression 17 is then mounted, as shown in FIG. 11, on the crown model 19 and the small holes 20, saddle 23, and clasp 11 and rest 12 portions of the pick-up impression 17 are coated with a release agent such as Kulzer's Micro-Film Separating Agent. After the release agent has been added, a pattern 25 is made, as shown in FIG. 11 by applying a layer of a pattern resin, such as, GC America Pattern Resin with a brush to the saddle 23 and pick-up impression 17. After the resin has hardened, the pattern 25 is trimmed. During the trimming, care must be taken to maintain the inside dimension 26 of the clasp 11 and lower surface of the rest 12. This is critical to achieving satisfactory results. After the pattern 25 has been trimmed, it is duplicated in metal by investment casting.

The metal model 27 of the clasp 11 and rest 12 is mounted, as shown in FIG. 12, on the crown model 19 and the crown is fitted to the model 27 of the clasp 11 and rest 12.

When the crown is returned, it should not be necessary to modify or adjust the partial denture when the crown is seated in the patient's mouth and the partial seated over the crown and other teeth.

From the foregoing it will be understood that my method for adapting a crown to an existing partial denture permits a patient to retain the partial while the crown is being fabricated at a dental lab. In doing so, the number of visits to a dentist is reduced and no longer is the patient's appearance or his eating ability impaired. Most importantly, the crown can be retrofit to the existing partial denture without losing the retention of the partial denture. Without my technique, many partial dentures must be remade or we find that their function is significantly compromised.

Although only a single embodiment of my invention has been described, it is not my intention to limit my invention to this embodiment, since other embodiments can be derived by changes in material, the arrangement of steps, and other changes known to ordinary persons skilled in the art without departing from the spirit thereof.

I claim:

1. In a method of the type wherein a crown is adapted to an existing clasp and rest of a partial denture, the improvement comprising the steps of: adding a dimensionally stable coping made from a light curing resin to a patient's tooth after said tooth has been prepared for said crown; applying a tray adhesive to an outer surface of said coping; fabricating an accurate pick-up impression made from a dimensionally stable polyvinyl material over said coping; returning a partial denture to said patient's mouth to embed said clasp and rest in said pick-up impression; removing portions of said pick-up impression to remove said clasp and rest from said pick-up impression; removing said clasp and rest from said pick-up impression; sending said pick-up impression with said coping to a dental laboratory for fabricating an accurate model of said clasp and rest; returning said partial denture to said patient's mouth for the patient's use during the time that said crown is being fabricated at a dental laboratory; fabricating an accurate model of the clasp and rest at said dental laboratory; and incorporating said clasp and rest model in a second model at the dental laboratory which is used for fabricating said crown.

2. The improvement as recited in claim 1 wherein said light curing resin is comprised of silicone dioxide.

3. The improvement as recited in claim 1 wherein said polyvinyl material is comprised of a vinyl polysiloxane.

4. A method for adapting a crown to a clasp and rest of an existing partial denture without depriving a patient of said partial denture during the time said crown is being fabricated at a dental laboratory, comprised of the steps of: preparing a tooth for a crown; fabricating a coping made from a stable low shrinkage light curing resin over said prepared tooth; returning said partial denture to said patient's mouth, said partial denture having a clasp surrounding said coping and a rest overlying said coping; providing a clearance between said coping and said clasp of about 1 to 1.5 millimeters; removing said partial denture from said patient's mouth; covering an outer surface of said coping with a tray adhesive; fabricating a pick-up impression made from a polyvinyl material over said coping; returning said partial denture to said patient's mouth before said pick-up impression sets up to completely embed said clasp and said rest in said pick-up impression; removing said partial denture, coping and pick-up impression from said patient's mouth; slicing away thin layers of said pick-up impression to expose said clasp and rest of said partial denture; removing said clasp and rest from said pick-up impression; sending said pick-up impression and coping to said dental laboratory for use during a fabrication of said crown; and returning said partial denture to the patient's mouth for said patient's use during said fabrication of said crown.

5. A method for adapting a crown to a clasp and rest of an existing partial denture comprised of the steps of: fabricating a coping made from a stable low shrinkage light curing silicone dioxide material over a tooth which has been prepared for a crown; covering an outer surface of said coping with a layer of a tray adhesive which is chemically compatible with said light curing material of said coping; fabricating a pick-up impression made from a vinyl polysiloxane material over said adhesive covered coping; returning a partial denture having a clasp and a rest to said patient's mouth before said pick-up impression sets up to completely to embed said clasp and said rest in said pick-up impression; slicing away thin layers of said pick-up impression to remove said clasp and rest from said pick-up impression; removing said clasp and rest from said pick-up impression; sending said pick-up impression and coping to a dental laboratory for use during a fabrication of said crown; and returning said partial denture to the patient's mouth.

6. The method as recited in claim 5 further comprising the step of allowing said pickup impression to set-up for about 1 to 1.5 minutes before said fabricating of said tray adhesive over said coated coping.

7. The method as recited in claim 5 further comprising the step of allowing said pick-up impression to set up for about 2 to 2.5 minutes after said clasp and said rest have been imbedded in said pick-up impression material.

8. The method as recited in claim 5 further comprising the step of fabricating an accurate model of said clasp and rest at said dental laboratory from said pick-up impression of said dental office.

9. A method for adapting a crown to a clasp and rest of an existing partial denture without depriving a patient of said partial denture during the time said crown is being fabricated at a dental laboratory, comprising the steps of: fabricating an accurate pick-up impression of said clasp and rest of said patient's partial denture in a dentist's office; using said pick-up impression to fabricate an accurate model of said clasp and rest in a dental laboratory; and incorporating said clasp and rest model at said dental laboratory in a second model which is used for fabricating said crown.

* * * * *